United States Patent [19]

Entwistle et al.

[11] 4,211,727
[45] Jul. 8, 1980

[54] REDUCTION OF CARBOXYLIC ACID HALIDES TO ALDEHYDES

[75] Inventors: Ian D. Entwistle, Sittingbourne; Robert A. W. Johnstone, Liverpool, both of England

[73] Assignee: Shell Oil Company, Houston, Tex.

[21] Appl. No.: 20,782

[22] Filed: Mar. 15, 1979

[51] Int. Cl.$^2$ .............................................. C07C 45/00
[52] U.S. Cl. ............................... 568/437; 260/465 R; 560/51; 560/124; 260/566 B; 568/423; 568/424; 568/488; 568/490; 568/420
[58] Field of Search ................ 260/599, 598, 600 R, 260/601 R, 602, 465 R; 560/124, 51

[56] References Cited

U.S. PATENT DOCUMENTS

| | | | |
|---|---|---|---|
| 3,076,033 | 1/1963 | Friedman et al. | 260/599 X |
| 3,147,272 | 9/1964 | Brown et al. | 260/599 X |
| 3,277,178 | 10/1966 | Brown | 260/599 X |

FOREIGN PATENT DOCUMENTS 1247783 9/1971 United Kingdom .

OTHER PUBLICATIONS

Yoon et al., Journal of the Korean Chem. Soc., vol. 20, No. 1 (1976), pp. 59-72.
Wiberg et al., Z. Naturforsch, 7B, (1952) 579-582.

*Primary Examiner*—Bernard Helfin

[57] ABSTRACT

Carboxylic acid halides are reduced to the corresponding aldehydes using zinc borohydride or cadmium borohydride as the reducing agent.

7 Claims, No Drawings

REDUCTION OF CARBOXYLIC ACID HALIDES TO ALDEHYDES

BACKGROUND OF THE INVENTION

1. Field of the Invention

The invention relates to a process for the reduction of carboxylic acid halides to aldehydes and to a reagent for the reduction.

2. Description of the Prior Art

A widely used process for the catalytic reduction of carboxylic acid chlorides to the corresponding aldehydes is the Rosenmund reduction. In this process, carboxylic acid chlorides are hydrogenated using a suitable catalyst, usually 5% palladium on barium sulfate, poisoned with a mixture of quinoline and sulfur to prevent further reduction to the alcohol. This process has the economic disadvantage that pressure equipment is required. An additional disadvantage is that certain functional groups other than the acid chloride group are reduced: for example, nitro groups are reduced to amino groups.

Most hydride reducing agents reduce carboxylic acid chlorides to the corresponding alcohols. However, at very low temperatures, for example $-80°$ C. to $-70°$ C., lithium tri-t-butoxyaluminum hydride and sodium borohydride may be used to reduce acid chlorides to the corresponding aldehydes. Certain complex hydride reducing agents can be used for the reduction of specific acid chlorides to aldehydes; for example, sodium trimethoxyborohydride reduces most acid chlorides to the corresponding aldehydes. Certain complex hydride reducing agents can be used for the reduction of specific acid chlorides to aldehydes; for example, sodium trimethoxyborohydride reduces most acid chlorides to the corresponding alcohol, but reduces triacetylshikimic acid chloride to the corresponding aldehyde.

SUMMARY OF THE INVENTION

We have now found a new method of reducing carboxylic acid halides, especially chlorides, to give the corresponding aldehyde, and a new reagent capable of performing this reduction.

The present invention provides a process for the reduction of a carboxylic acid halide to the corresponding aldehyde, which comprises reducing the acid halide using zinc borohydride or cadmium borohydride as reducing agent.

The reducing agent is suitably used in the form of a solution prepared by mixing a solution or suspension of a zinc or cadmium salt with a solution or suspension of sodium borohydride. The invention therefore also provides a process for the reduction of a carboxylic acid halide to the corresponding aldehyde, which comprises reducing the acid halide using zinc or cadmium borohydride produced in situ.

Preferably the acid halide is an acid bromide or, especially, an acid chloride.

The alkali metal borohydride may be lithium, sodium or potassium borohydride and is preferably potassium or sodium borohydride. Sodium borohydride is most preferred.

The cadmium halide may be cadmium fluoride, chloride, bromide or iodide and is advantageously cadmium chloride or cadmium bromide. Cadmium chloride is most preferred.

Cadmium borohydride is a novel compound and this invention also relates to cadmium borohydride per se.

Preferably a solution of cadmium borohydride is prepared by the reaction of cadmium chloride with sodium borohydride in a solvent system which is capable of dissolving at least small quantities of the reactants. Complete solubility of the reactants is not required. Since cadmium chloride and sodium borohydride are relatively insoluble in many common solvents, a mixture of solvents is generally required. Aprotic, polar solvents are required, but these need not be dried as the reaction producing cadmium borohydride and the subsequent reaction with an acid halide will proceed in the presence of traces of water. A solvent mixture of acetonitrile with a co-solvent, for example diglyme, hexamethylphosphoramide or, preferably, diethylformamide, has proved to be especially useful.

The reduction process of the invention may, if the acid halide to be reduced is a liquid, be carried out in the absence of a solvent. For example: solid zinc borohydride may be added to the liquid acid halide. Preferably however, an aprotic polar solvent or mixture of such solvents is used such as those described above.

Suitably a solution of the reducing agent, for example cadmium borohydride in a mixture of solvents, is prepared, and a solution of the acid halide in one or more of the solvents present in the mixture is added.

To prepare a solution of the reducing agent, preferably a slight excess of one of the reagents is used. For example, 5 to 10% molar excess of a cadmium or zinc salt may be added to sodium borohydride. Excess sodium borohydride may be added, but this may be undesirable as the unreacted sodium borohydride may affect the course of the subsequent reduction reaction, for example, by increasing the yield of alcohol at the expense of the yield of aldehyde.

One specific method of preparing the solution of cadmium borohydride is as follows: Cadmium chloride was recrystallized from dimethylformamide to give a solid adduct thought to have the empirical formula $CdCl_2.1.5$ DMF. One mol of this complex was added to a 1:1 mix of acetonitrile and dimethylformamide, and 2 mol of $NaBH_4$ were added. The resulting solution contained approximately 0.14 m mol of cadmium borohydride per milliliter of solution. The bulk solution stored well at $0°$ with a white solid separating out slowly.

This white solid has now been shown not to be sodium chloride, suggesting that the cadmium borohydride reducing agent is not present as $Cd(BH_4)_2$ per se, but may be present in a complex such as $Na_2[CdCl_2(BH_4)_2]$. However this is a tentative theory which is not yet proven.

When performing the reduction, suitably the reducing agent is used in slight molar excess over the acid halide, for example 5 to 10% molar excess.

The reduction process of the invention has the advantage that, unlike many hydride reductions, extremely low temperatures are not required. The process of the invention may be performed, for example, at a temperature in the range of from $-35°$ C. to $0°$ C., at which temperature satisfactory yields are obtained. For comparison, sodium borohydride, which is generally regarded as an agent for the reduction of carboxylic acid chlorides to alcohols, will reduce carboxylic acid chlorides to aldehydes, but yields comparable with those obtained using cadmium borohydride are only obtained at temperatures of around $-80°$ C. Cadmium borohydride will produce the aldehyde at temperatures of greater than 0° C., but yields of by-products, for example the alcohol and the anhydride, increase with temperature.

A further advantage of the use of cadmium borohydride as a reducing agent is that it appears to be relatively selective in its action. For example, ester groups, cyano groups, nitro groups, chlorine atoms and carbon-carbon double bonds are not reduced. Expensive pressure equipment is of course not required. The selectivity of the reduction process to halogen substituents other than that in the carboxy bromide group of the carboxylic acid bromide is particularly worthy of note. Even relatively reactive halogen, e.g. bromo and chloro, substituents in haloalkyl and arylhaloalkyl groups have been found to be unaffected by the reaction conditions of the process of the invention.

The process of the invention may be used for the reduction of aromatic, cycloaliphatic or aliphatic acid halides. The reaction may be represented by the equation:

$$R . CO . Hal \xrightarrow{BH_4^-} R . CO . H$$

R may represent, for example, an aryl or aralkyl group, for example a phenyl or benzyl group; an alkyl, alkenyl or alkynyl group, suitably having up to 10 carbon atoms, for example an octyl group or a 1-propenyl group; or a cycloalkyl group, suitably having from 3 to 6 ring carbon atoms, for example a cyclopropyl or a cyclohexyl group. Any of the above groups may be substituted by one or more substituents, for example an aryl or cycloalkyl ring may be substituted by one or more alkyl, alkoxy, cyano, nitro, or alkoxycarbonyl groups or halogen atoms, and an alkyl, alkenyl or alkynyl group may be substituted by alkoxy, cyano or alkoxycarbonyl groups or halogen atoms.

Preferably R may represent (i) a cyclopropyl group of formula

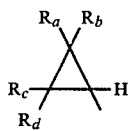

wherein $R_a$ and $R_b$ each represent an alkyl group having from 1 to 6 carbon atoms, especially methyl, or a halogen atom of atomic number 9-35, inclusive, especially a chlorine atom; or $R_a$ and $R_b$ together represent an alkylene group having from 2 to 6, especially 3, carbon atoms; or when $R_a$ represents a hydrogen atom then $R_b$ represents an alkenyl group having from 2 to 6 carbon atoms, especially an isobutenyl group, or an haloalkenyl group having from 2 to 6 carbon atoms and from 1 to 3 chlorine or bromine atoms, especially a mono- or dichlorovinyl group; $R_c$ and $R_d$ each represent an alkyl group having 1 to 6 carbon atoms, especially methyl, or when $R_c$ is hydrogen then $R_d$ is an alkenyl group having from 2 to 6 carbon atoms, especially an isobutenyl group, or an haloalkenyl group having from 2 to 6 carbon atoms and from 1 to 3 chlorine or bromine atoms, especially a mono- or dichlorovinyl group; or $R_c$ and $R_d$ together represent an alkylene group having from 2 to 6, especially 3, carbon atoms; or (ii) a benzyl group of formula

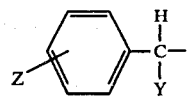

wherein Z represents a halogen atom of atomic number 9-35, inclusive, preferably a chlorine atom, or an alkoxy group of 1 to 4 carbon atoms, e.g. methoxy, and Y represents an alkyl group of 1 to 6 carbon atoms, especially a branched chain group such as an isopropyl group.

The process of the invention may be usefully applied in the preparation of aldehydes containing cyclopropyl groups. Certain aldehydes are useful in the synthesis of biologically active molecules, for example of the pyrethroid ester type from 3-phenoxybenzaldehyde.

The following Examples illustrate the invention.

EXAMPLE 1

Preparation of Cadmium Borohydride Solution

Cadmium chloride was recrystallized from dimethylformamide; it is thought that this solid has the empirical formula $CdCl_2.1.5$ DMF. One mol of this complex was added to a 1:1 mix of acetonitrile and dimethylformamide, and 2 mol of $NaBH_4$ were added. The resulting solution contained approximately 0.14 m mol of $Cd(BH_4)_2$ per milliliter of solution. The bulk solution stored well at 0° C., with white solid NaCl separating out slowly.

EXAMPLE 2

This Example illustrates the improved yields obtained in the reduction of a range of carboxylic acid chlorides to the corresponding aldehydes using cadmium borohydride as reducing agent.

A solution of $NaBH_4$ (0.76 g) in dimethylformamide (5 ml) and acetonitrile (60 ml) was added over 10 minutes to a stirred suspension of 4.6 g (25 m mol) $CdCl_2$ in acetonitrile (25 ml) at 0° C. The mixture was stirred for a further 10 minutes at 0° to 3° C. and then cooled to −35° C. A solution of 20 m mol acid chloride in 20 ml acetonitrile was added over a quarter of an hour. After stirring for a further 10 minutes, the temperature was allowed to rise to room temperature and the mixture was poured onto 2 N HCl (50 ml) and ice (50 g).

The aldehyde produced was isolated as its hydrazone by adding a saturated solution of 2,4-dinitrophenylhydrazine (20 ml) to the acidified solution. After warming over a steam bath, the yellow/orange precipitate of the 2,4-dinitrophenylhydrazine of the aldehyde was filtered off.

The results for various starting materials are listed in the following table, which also lists, for comparison, results obtained using sodium borohydride alone (i.e. without addition of $CdCl_2$) under the same reaction conditions. The comparison results show that in general, yields obtained using cadmium borohydride are approximately double the yields obtained using sodium borohydride.

| Starting Acid Chloride | 2,4-dinitrophenylhydrazone of the Resulting Aldehyde | | |
|---|---|---|---|
| | Using Cd(BH₄)₂ | | Using NaBH₄ (for comparison only) |
| | % Yield (calculated on starting acid chloride) | M.P. (°C.) | % Yield (calculated on starting acid chloride) |
| (CH₃)₂CH—CO.Cl | 62 | 176–177 | 32 |
| cis-cyclopropane-1,2-(CO.Cl)(CO₂C₂H₅) | 50 | 157–159 | 23 |
| C₆H₁₁—CO.Cl (cyclohexanecarbonyl chloride) | 24 | 165–166 | 7.5 |
| (CH₃)₂C(CH=CCl₂)—CO.Cl derivative | 74 | 124–128 | 43.6 |
| Cl—C₆H₄—O—CH(CH(CH₃)₂)—CO.Cl | 61 | | 25 |
| C₆H₅—O—C₆H₄—CO.Cl | 81 | 185–187 | 40.5 |
| CH₃.(CH₂)₁₆.CO.Cl | High yield of polymer formed from aldehyde | | |

EXAMPLE 3

This Example illustrates the yields obtained in the cadmium borohydride reduction of a range of aromatic and aliphatic acid chlorides, many containing substituents sensitive to other reducing agents.

Seventy-six mg (2 m mol) NaBH₄ were dissolved in 10 ml acetonitrile and 0.35 ml hexamethylphosphoramide. Three hundred and seventy mg cadmium chloride recrystallized from dimethylformamide were added; this amount corresponded to 1 m mol assuming a molecular formula of CaCl₂.2.5 DMF. The reaction mixture was cooled to −10° C. to −5° C., and 2 m mol acid chloride in 2–3 ml acetonitrile were added rapidly and the solution stirred well for 5 minutes. Dilute HCl was added to decompose excess reducing agent. Excess 2,4-dinitrophenylhydrazine solution was added and the reaction mixture was heated on a water bath for a few minutes to complete the reaction. The precipitated 2,4-dinitrophenylhydrazone was filtered, washed and dried; in many cases, satisfactory purity was obtained without recrystallization. The results are shown in the following table.

| Starting Acid Chloride | 2,4-dinitrophenylhydrazone of the Resulting Aldehyde | | |
|---|---|---|---|
| | % Yield (calculated on starting acid chloride) | M.P. (°C.)* | Literature M.P. (°C.)* |
| Benzoyl chloride | 76 | 241–242 | 237 (acetic acid) |
| 4-methylbenzoyl chloride | 89 | 238–240 | 233–234 |
| 4-chlorobenzoyl chloride | 74 | 272 | 270–271 (ethanol) |
| 4-nitrobenzoyl chloride | 71 | 317–318 | 320 (xylene) |
| 4-methoxybenzoyl chloride | 63 | 251–252 | 253–254 (acetic acid) |
| 4-cyanobenzoyl chloride | 67 | 307–308 (acetic acid) | 295–298 (acetic acid) |
| 2-methylbenzoyl chloride | 60 | 190–192 | 190–193 |
| 2-bromobenzoyl chloride | 62 | 199–200 | 203 (xylene) |
| 2-methoxycarbonylbenzoyl chloride | 52 | 242–243 (xylene) | — |
| trans-cinnamoyl chloride | 71 | 253–254 | 255 acid) |
| phenylacetyl chloride | 58 | 115–117 (ethanol/benzene) | 125–126 (ethanol/benzene) |
| octanoyl chloride | 56 | 103 (ethanol) | 106 |
| crotonyl chloride | 54 | 182–184 (ethyl acetate/ethanol) | 184–185 |
| pivaloyl chloride | 32 | 209–210 (ethyl acetate/ | 210 |

| | 2,4-dinitrophenylhydrazone of the Resulting Aldehyde | |
|---|---|---|
| Starting Acid Chloride | % Yield (calculated on starting acid chloride) | Literature M.P. (°C.)* |
| | M.P. (°C.)* ethanol) | |

*The solvent used for recrystallization of the 2,4-dinitrophenyl-hydrazine, if recrystallization was performed, is shown in brackets.

EXAMPLE 4

Carboxylic acid bromides were reduced to the corresponding aldehydes by the following procedure. A solution of sodium borohydride (0.76 g) in dimethylformamide (5 ml) and acetonitrile (60 ml) was added over 10 minutes to a stirred suspension of cadmium chloride (4.6 g, 25 m mol) in acetonitrile (25 ml) at 0° C. The mixture was stirred for a further 10 minutes at 0° to 3° C. and then cooled to −35° C. A solution of the carboxylic acid bromide (20 m mol) in acetonitrile was added over a quarter of an hour. After stirring for a further 10 minutes, the temperature was allowed to rise to room temperature, and the mixture was poured onto 2 N HCl (50 ml) and ice (50 g).

The aldehyde produced was isolated as its hydrazone by adding a saturated solution of 2,4-dinitrophenylhydrazine (200 ml) to the acidified solution. After warming over a steam bath, the yellow/orange precipitate of the 2,4-dinitrophenylhydrazone was filtered off.

The results obtained are given in the following table:

| | 2,4-dinitrophenylhydrazone of the resulting aldehyde | |
|---|---|---|
| Starting Acid Bromide | % Yield (based on starting acid bromide) | Melting Point (0° C.) |
| cis-H,H / COBr, COOC$_2$H$_5$ cyclopropane | 45 | 158°–159° C. |
| C$_6$H$_5$—COBr | 10 | 165°–166° C. |
| C$_6$H$_5$—COBr | 80 | 241°–242° C. |

We claim:
1. A process for the reduction of a carboxylic acid chloride to the corresponding aldehyde which comprises reducing the acid chloride using a complex of cadmium borohydride prepared by mixing a solution or suspension of a cadmium salt with a solution or suspension of sodium borohydride as the reducing agent and at a temperature in the range of from about 35° C. to 0° C.
2. A process according to claim 1 wherein the solution is prepared using an aprotic, polar solvent or a mixture of such solvents.
3. A process according to claim 2 wherein the solvent is a mixture of acetonitrile with diglyme; hexamethylphosphoramide or dimethylformamide.
4. A process according to claim 1 wherein the cadmium borohydride is produced in situ.
5. A process according to claim 1 which is conducted in the presence of an aprotic, polar solvent.
6. A process according to claim 1 wherein the acid chloride is selected from cyclopropanecarboxylic acid chloride, cis-2-ethoxycarbonyl cyclopropanecarboxylic acid chloride, cyclohexanecarboxylic acid chloride, 2,2-dimethyl-3-(2,2-dichlorovinyl)cyclopropanecarboxylic acid chloride, α-isopropyl-p-chlorophenylacetic acid chloride and 3-phenoxybenzoic acid chloride.
7. A process according to claim 6 wherein the acid chloride is 3-phenoxybenzoic acid chloride.

* * * * *